(12) United States Patent
Teplitzky et al.

(10) Patent No.: US 11,133,112 B2
(45) Date of Patent: Sep. 28, 2021

(54) MULTI-CHANNEL AND WITH RHYTHM TRANSFER LEARNING

(71) Applicant: Preventice Technologies, inc., Rochester, MN (US)

(72) Inventors: Benjamin Adam Teplitzky, Minneapolis, MN (US); Michael Thomas Edward McRoberts, Mazeppa, MN (US); Pooja Rajiv Mehta, Houston, TX (US)

(73) Assignee: Preventice Technologies, Inc., Rochester, MN (US)

( * ) Notice: Subject to any disclaimer, the term of this patent is extended or adjusted under 35 U.S.C. 154(b) by 0 days.

(21) Appl. No.: 16/695,534

(22) Filed: Nov. 26, 2019

(65) Prior Publication Data

US 2020/0176122 A1  Jun. 4, 2020

Related U.S. Application Data

(60) Provisional application No. 62/773,817, filed on Nov. 30, 2018.

(51) Int. Cl.
*G16H 50/70* (2018.01)
*G06N 3/04* (2006.01)
*G06N 3/08* (2006.01)

(52) U.S. Cl.
CPC .............. *G16H 50/70* (2018.01); *G06N 3/04* (2013.01); *G06N 3/08* (2013.01)

(58) Field of Classification Search
CPC ............. G16H 50/70; G06N 3/04; G06N 3/08
See application file for complete search history.

(56) References Cited

U.S. PATENT DOCUMENTS 9,161,705 B2  10/2015 Tamil et al.
10,426,364 B2  10/2019 Rapin et al.
(Continued)

FOREIGN PATENT DOCUMENTS

WO   2019186050 A1   10/2019
WO   2019231808 A1   12/2019

OTHER PUBLICATIONS

Rajpurkar et al., "Cardiologist-Level Arrhythmia Detection with Convolutional Neural Networks," in arXiv preprint arXiv: 1707.01836 (2017). (Year: 2017).*

(Continued)

*Primary Examiner* — Kamran Afshar
*Assistant Examiner* — Ryan C Vaughn
(74) *Attorney, Agent, or Firm* — Patterson + Sheridan, LLP

(57) ABSTRACT

Techniques for classifying cardiac events in electrocardiogram (ECG) data. A feature set is generated by analyzing ECG data for a patient using a first phase in a machine learning architecture. A first cardiac event in the ECG data is classified based on the feature set, using the first phase in the machine learning architecture. A second cardiac event in the ECG data is classified based on the classified first cardiac event and the feature set, using a second phase in the machine learning architecture. The second cardiac event overlaps at least partially in time with the first cardiac event. Further, a plurality of feature sets, corresponding to a plurality channels of ECG data, are generated using paths in a machine learning architecture. A cardiac event in the ECG data is classified using the machine learning architecture based on the plurality of feature sets.

16 Claims, 11 Drawing Sheets

(56) References Cited

U.S. PATENT DOCUMENTS

| | | | |
|---|---|---|---|
| 10,463,314 B1* | 11/2019 | Najarian | A61B 5/7275 |
| 10,758,139 B2 | 9/2020 | Rapin et al. | |
| 10,779,744 B2 | 9/2020 | Rapin et al. | |
| 2008/0103403 A1* | 5/2008 | Cohen | G16H 50/20 |
| | | | 600/509 |
| 2017/0032221 A1* | 2/2017 | Wu | A61B 7/04 |
| 2017/0112401 A1* | 4/2017 | Rapin | G16H 50/20 |
| 2018/0032689 A1 | 2/2018 | Kiranyaz et al. | |
| 2018/0249964 A1* | 9/2018 | Qian | A61B 5/0255 |
| 2019/0090769 A1* | 3/2019 | Boleyn | A61B 5/0404 |
| 2019/0133468 A1* | 5/2019 | Aliamiri | A61B 5/02416 |
| 2019/0150794 A1* | 5/2019 | Vrudhula | G06N 3/0454 |

OTHER PUBLICATIONS

Vishwa et al., "Clasification [sic] of Arrhythmic ECG Data Using Machine Learning Techniques," in 1.4 Intl. J. Artificial Intelligence and Interactive Multimedia 67-70 (2011). (Year: 2011).*

Xiong et al., "Robust ECG Signal Classification for Detection of Atrial Fibrillation Using a Novel Neural Network," in 44 Computing in Cardiology 1-4 (2017). (Year: 2017).*

Hosseini et al., "A Multi-Stage Neural Network Classifier for ECG Events," in 2001 Proc 23rd Annual EMBS Intl. Conf. 1672-75 (2001). (Year: 2001).*

Liu, "Probabilistic Siamese Network for Learning Representations," master's thesis, U. Toronto (2013). (Year: 2013).*

Kim, "Arrhythmia Classification in Multi-Channel ECG Signals Using Deep Neural Networks," master's thesis, U. Cal. Berkeley (2018). (Year: 2018).*

Xiao et al., "A Deep Learning Approach to Examine Ischemic ST Changes in Ambulatory ECG Recordings," in AMIA Summits on Translational Sci. Proc. 256-62 (2018). (Year: 2018).*

Written Opinon for PCT/US2019/063203 dated Jun. 23, 2020.

Kiranyaz S et al., "Real-Time Patient-Specific ECG Classification by 1-D Convolutional Neural Networks," IEEE Transactions on Biomedical Engineering, vol. 63, No. 3, Mar. 1, 2016, pp. 664-675.

Sodmann P et al., "A Convolutional Neural Network for ECG Annotation as the Basic for Classification of Cardiac Rhythms," Physiological Measurement, vol. 39, No. 10, Oct. 24, 2048, p. 104005.

PCT International Preliminary Report on Patentability for Application No. PCT/US2019/063203 dated May 25, 2021.

* cited by examiner

MULTI-CHANNEL AND WITH RHYTHM TRANSFER LEARNING

CROSS-REFERENCE TO RELATED APPLICATIONS

This application claims benefit to U.S. provisional application Ser. No. 62/773,817 filed on Nov. 30, 2018. The aforementioned related patent application is herein incorporated by reference in its entirety.

BACKGROUND

Portable monitoring devices for collecting biometric data are becoming increasingly common in diagnosing and treating medical conditions in patients. Mobile cardiac telemetry (MCT) is one example of this. MCT empowers physicians with valuable information regarding the occurrence and regularity of a variety of heart conditions and irregularities. ECG data collected using MCT can be analyzed to detect a variety of cardiac conditions, including various irregular heartbeats and heart rhythms.

BRIEF DESCRIPTION OF THE DRAWINGS

So that the manner in which the features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit of other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DESCRIPTION OF EXAMPLE EMBODIMENTS

Overview

Figure 1:
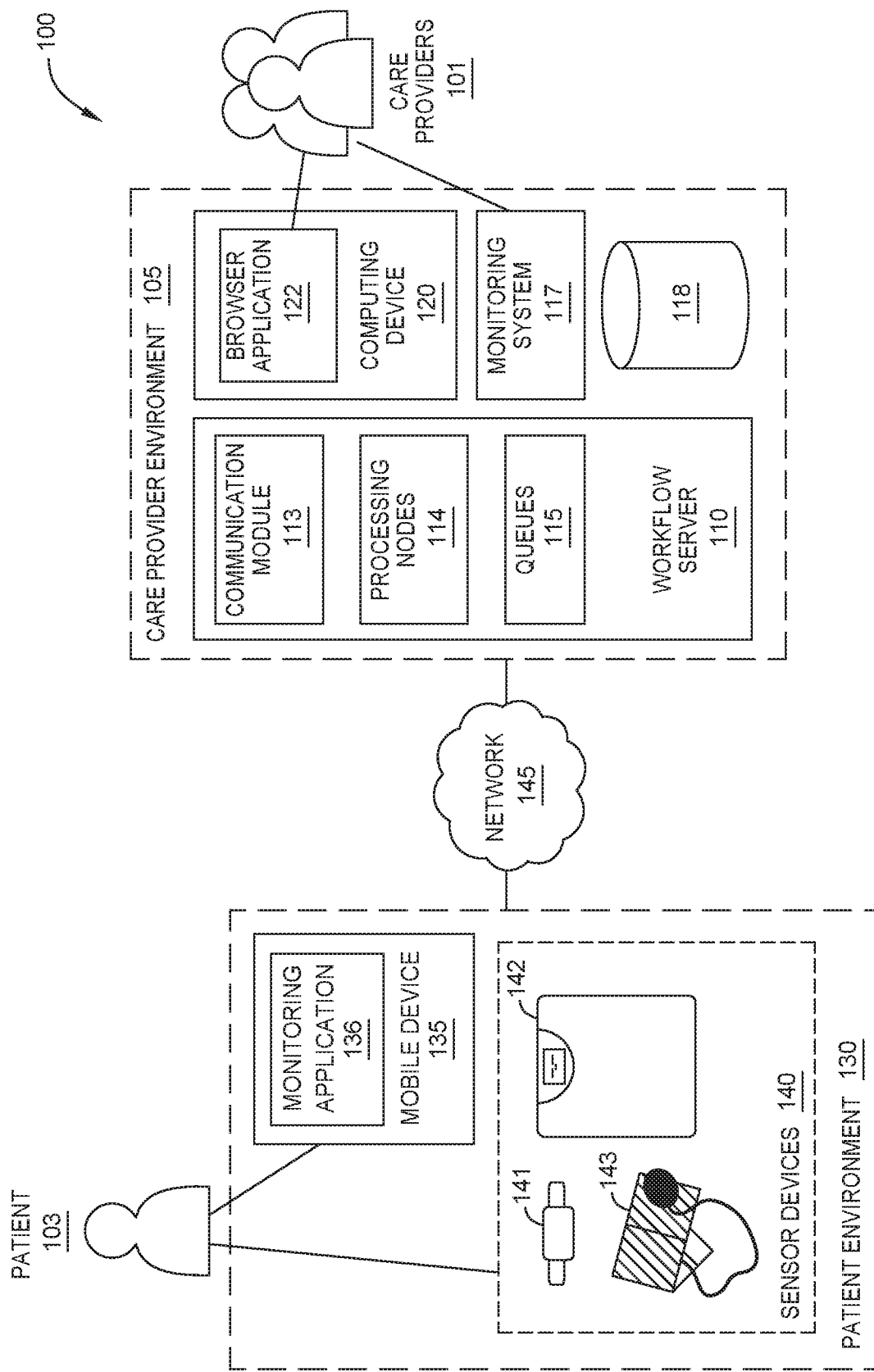
FIG. 1 illustrates an example computing environment, according to one embodiment.

An embodiment described herein is a computer-implemented method for classifying cardiac events. The method includes generating a feature set by analyzing electrocardiogram (ECG) data for a patient using a first phase in a machine learning architecture. The method further includes classifying a first cardiac event in the ECG data, based on the feature set, using the first phase in the machine learning architecture. The method further includes classifying a second cardiac event in the ECG data, based on the classified first cardiac event and the feature set, using a second phase in the machine learning architecture. The second cardiac event overlaps at least partially in time with the first cardiac event.

A further embodiment described herein is a computer-implemented method for classifying a cardiac event. The method includes receiving a plurality of channels of electrocardiogram (ECG) data relating to a patient. The method further includes generating a plurality of feature sets, each corresponding to a respective one of the plurality of channels of ECG data. Each feature set is generated using a respective path in a machine learning architecture. The method further includes classifying a cardiac event in the ECG data, using the machine learning architecture, based on the plurality of feature sets.

A further embodiment described herein is a system for classifying cardiac events. The system includes a processor and a memory storing a program, which, when executed on the processor, performs an operation. The operation includes receiving a plurality of channels of electrocardiogram (ECG) data relating to a patient. The operation further includes generating a plurality of feature sets, each corresponding to a respective one of the plurality of channels of ECG data. Each feature set is generated using a respective path in a machine learning architecture. The operation further includes classifying a first cardiac event in the ECG data, based on at least one of the plurality of feature sets, using a first phase in the machine learning architecture. The operation further includes classifying a second cardiac event in the ECG data, based on the classified first cardiac event and the at least one of the plurality of feature sets, using a second phase in the machine learning architecture. The second cardiac event overlaps at least partially in time with the first cardiac event.

Example Embodiments

Interpreting patient ECG data can be difficult and time consuming. Deep learning techniques can allow for accurate and speedy identification of cardiac events (e.g., abnormal heart beats and heart rhythms) in ECG data.

In an embodiment, ECG data for a patient can reflect multiple parallel cardiac rhythms. For example, ECG data can reflect a patient experiencing a main rhythm (e.g., a normal sinus rhythm or an atrial fibrillation) in parallel with a "with rhythm" (e.g., intraventricular conduction delay (IVCD) and first-degree heart block). The "with rhythm" can occur simultaneously with the underlying main rhythm, and the ECG data can reflect both rhythms. Further, in some circumstances a patient can experience multiple "with rhythms" in parallel to the main rhythm. The ECG data can reflect all of these parallel rhythms.

In an embodiment, deep learning techniques can be used to build an accurate and fast algorithm that detects and classifies "with rhythms" along with main rhythms. This can improve the accuracy and speed of detecting these rhythms, allowing for more accurate (and rapid) medical treatment and alerts for patients (e.g., providing medical treatment to a patient, providing notification to a care provider, or providing an alert to a monitoring service). For example, transfer learning techniques can be used. In one example, a deep learning model to detect the main rhythm can be designed and trained using supervised learning (e.g., using pre-labeled data). The deep learning model can be extended to also classify "with rhythms." In an embodiment, multiple classifier networks can be designed and trained, each intended to classify a particular "with rhythm" based on both the output of the main rhythm classifier and the underlying ECG data. These classifiers can be used, in parallel, to simultaneously identify multiple "with rhythms."

As another example, a patient may wear a cardiac monitoring device that detects multiple channels of ECG data. For example, each sensor pair on the device may detect a different channel of ECG data. That is, a device might include 1 sensor pair for detecting 1 channel of data, 3 sensor pairs for detecting 3 channels of data, 12 sensor pairs for detecting 12 channels of data, or even 64 sensor pairs for detecting 64 channels of data. As another example, sensor pairs can be used to detect more data channels than there are sensors. For example, a device with 3 sensors may be able to calculate more than 3 channels of data (e.g., 6 data channels). A device with 5 or more sensors may be able to calculate even more channels. In an embodiment, each of these channels captures slightly different aspects of electrical propagation through the heart, and will therefore contain time-synced, but slightly different, electro-physical representations of cardiac activity.

Deep learning techniques can be used to identify cardiac events (e.g., rhythms or beats) using these multi-channel data. For example, in an embodiment and as discussed further below, transfer learning techniques can be used to leverage single channel ECG classifiers and create a multi-channel classifier. This can have numerous advantages, including, for example, improved accuracy, improved redundancy, and improved training of the machine learning model. Classified rhythms or beats can be provided to a patient, care provider, or monitoring service, and used in medical treatment of the patient.

FIG. 1 illustrates an example computing environment 100, according to one embodiment. As shown, the computing environment 100 may include a care provider environment 105 and a patient environment 130, each connected to one another via a network 145. The care provider environment 105 and the patient environment 130 allow a care provider 101 (e.g., a technician, nurse, physician, etc.) to monitor biometric data generated by the patient 103.

The care provider environment 105 includes a workflow server 110, a computing device 120, monitoring system 117 and data repository 118. Each of the workflow server 110, the computing device 120, and the monitoring system 117 may be a dedicated computing system or a virtual computer instance (e.g., executing in a cloud computing platform). A care provider 101 may use the computing device 120 to access (e.g., via a browser application 122, a native application on device 120, etc.) a user interface (UI) hosted by the monitoring system 117.

Of note, although shown as a single entity, the data repository 118 can represent multiple, separate data stores (e.g., relational databases). Moreover, these data stores can span multiple computing nodes. To this end, the separate data stores could be made to function as a single data store (e.g., through data replication techniques and through the use of load balancers). As such, the data repository 118 is representative of any sort of data store on any number of computing systems, consistent with the functionality described herein.

Additionally, although not shown, the data repository 118 may store data from and/or service requests from various other entities, such as third party applications, partners and affiliates, electronic medical record systems, external monitoring devices and products, analytics engines, data consolidator applications, and so on. More generally, it is contemplated that the data repository 118 and, more generally, other elements within the care provider environment 105, can interact with any number of different data originators and receipts, consistent with the functionality described herein. As such, the computing environment 100 is provided merely for illustrative purposes only and without limitation.

The workflow server 110 includes applications and data executed to identify and handle health events corresponding to the patient 103. As shown, workflow server 110 includes a communication module 113, processing nodes 114, and queues 115. In one embodiment, the processing nodes 114 are software code or applications that perform a predetermined task or action on received data (e.g., health events). The workflow server 110 evaluates data received from the patient environment 130 using a set of interconnected processing nodes 114 and the queues 115 which form a workflow. As the biometric data or health events are received from the patient environment 130, the workflow may classify (or reclassify) the data to identify a type of the health event—e.g., presentation or notification to patient/care provider, suppression, classification, aggregation, computation, prioritization/triage, and the like. For example, different types of data received from the patient environment 130 may trigger different types of health events—e.g., an irregular heartbeat may trigger a cardiac event, while a signal indicating an electrode has become detached triggers a maintenance event. In one embodiment, at least one sensor device 140 within the patient environment 130 or a monitoring application 136 installed as part of a mobile device 135 within the patient environment 130 may have performed an initial classification of the data or health events. Nonetheless, the workflow server 110 may evaluate the biometric data (or maintenance data) to confirm that this initial classification was correct.

Each type of health event may take a different path through the workflow. That is, different health events may traverse the processing nodes 114 and the queues 115 using different paths. For example, a cardiac event may be evaluated using different processing nodes 114 in the server 110 than a maintenance event. Furthermore, paths through the workflow for the same health event may differ based on a variety of factors such as the severity of the health event, age of the patient 103, other symptoms exhibited by the patient 103, medication taken by the patient 103, and the like. For example, a high priority cardiac event may skip one or more of the processing nodes 114 or the queues 115 and be immediately displayed to the care provider 101 using the monitoring system 117.

The communication module 113 permits the workflow server 110 to receive the data from the patient environment 130 and transmit data to the care providers 101. The communication module 113 may receive data from the at least one sensor device 140 which is used to identify a health event and a corresponding path through interconnected ones of the processing nodes 114 and the queues 115. The communication module 113 helps the care providers 101 complete the workflow by use of the monitoring system 117 and the computing device 120. Moreover, in addition to receiving the data from the patient environment 130, the communication module 113 may enable the workflow server 110 to transmit requests or instructions to the patient environment 130 such as asking the patient 103 if she has any symptoms or instructing the patient 103 to reattach a disconnected electrode (not shown) of the at least one sensor device 140.

In one embodiment, a path used by a health event to traverse the workflow server 110 may include processing nodes 114 that process the health event without user intervention as well as the processing nodes 114 that require input from the care providers 101. For example, one of the processing nodes 114 may filter or screen a health event to determine in what queue to place the event, compare the event to one or more rules to determine an action to perform, or store the event. Alternatively, others of the processing nodes 114 may require the care provider 101 to perform an action or provide instructions. For example, the monitoring system 117 may generate a user interface (UI) for a health event which is then displayed to the care provider 101 by the browser application 122. Once the care provider 101 performs an action (e.g., confirms the classification of the event or agrees with an action suggested by the workflow server 110), the remaining operations of the workflow are performed—e.g., send a notification to the patient 103, log the event in the history of the patient 103, route the event to a different one of the care providers 101, reclassify the health event (if the care provider 101 indicated the initial classification was incorrect), or prioritize or triage the health event.

With continued reference to FIG. 1, the patient environment 130 includes the mobile device 135 and the at least one sensor device 140. The mobile device 135 includes the monitoring application 136 which permits communication between the at least one sensor device 140 and the care provider environment 105 via the network 145. The monitoring application 136 may configure the at least one sensor device 140 (e.g., IoT devices) to monitor biometric data of the one or more patients 103 as specified by a care plan. For example, the monitoring application 136 could configure logic on a heart rate monitoring device worn by the patient to monitor the patient's heart rate. In turn, the monitoring application 136 can send the heart rate data to the workflow server 110 which determines if a heath event is triggered, and if so, executes a workflow to process the event as described above. In another embodiment, the heart rate monitoring device, upon detecting that a threshold condition has been satisfied, could generate and transmit a health event to the mobile device 135, which in turn transmits the health event to the workflow server 110 for processing. However, in other embodiments, some of the tasks performed by the workflow server 110 may be performed by the mobile device 135. That is, the workflow may include tasks performed by the mobile device 135 or the at least one sensor device 140 as well as tasks performed by the workflow server 110.

In one embodiment, the monitoring application 136 receives environmental data from the at least one sensor device 140. Generally, the environmental data informs the monitoring application 136 of environmental conditions in an area proximate to the at least one sensor device 140 and the user—e.g., a room in which the user is located. For example, the at least one sensor device 140 may detect an air quality or pollen count for the patient 103 having a respiratory ailment. In another example, the at least one sensor device 140 may track the user's movements or actions in an environment such as how many times at night the patient 103 goes to the bathroom or if the patient 103 is tossing and turning at night. This environmental data can then be used by the monitoring application 136 by itself, or in combination with the biometric data, to trigger health events which are processed by the workflow server 110.

In one embodiment, the monitoring application 136 may use an output device (e.g., a display or audio system) on the mobile device 135 to provide information to the patient 103. For example, when executing a workflow, one of the processing nodes 114 may ask the patient 103 if she is experiencing any symptoms. To obtain feedback from the patient 103, the monitoring application 136 may display a user interface (UI) on the mobile device 135 which permits the patient 103 to list symptoms. Moreover, the monitoring application 136 may also display general information related to a care plan or the at least one sensor device 140 such as the patient's heart rate or weight, status of the at least one sensor device 140, etc.

In one embodiment, the at least one sensor device 140 interacts with the monitoring application 136 and assists the patient 103 in reporting patient vitals and other information to the care provider environment 105. As shown, the at least one sensor device 140 may include a body sensor 141, a weighing scale 142, and a blood pressure cuff 143. Each of the at least one sensor device 140 may capture different vitals of the patient 103. For example, when applied to a body of patient 103, the body sensor 141 captures biometric data (e.g., heart rate, ECG data, etc.) in real-time. In addition, each of the at least one sensor device 140 may be configured to transmit body-related metrics electronically to the monitoring application 136 on the mobile device 135. In turn, the monitoring application 136 sends the captured metrics to the workflow server 110 which can be used to trigger health events which are processed using the processing nodes 114 and the queues 115.

In one embodiment, upon detecting an observation threshold has been reached, the at least one sensor device 140 performs an initial classification of the health event. In a particular embodiment, the mobile device 135 is configured to perform the initial classification of the health event. For example, the body sensor 141, upon detecting that ECG data collected from the patient 103 indicates an erratic heart behavior, could classify the health event as a cardiac event. This initial classification of the health event, along with the relevant ECG data (e.g., ECG data including a predetermined length of time before and after the event), could be transmitted to the mobile device 135 (e.g., over a Bluetooth® communications link) and the monitoring application 136 subsequently forwards the ECG data and the health event data on to the workflow server 110 over the network 145 (e.g., the Internet). Alternatively, instead of classifying the data, the monitoring application 136 may forward the raw, unprocessed sensor data to the workflow server 110 which uses one of the processing nodes 114 to identify and classify health events which are then processed in the workflow server 110.

Figure 2:
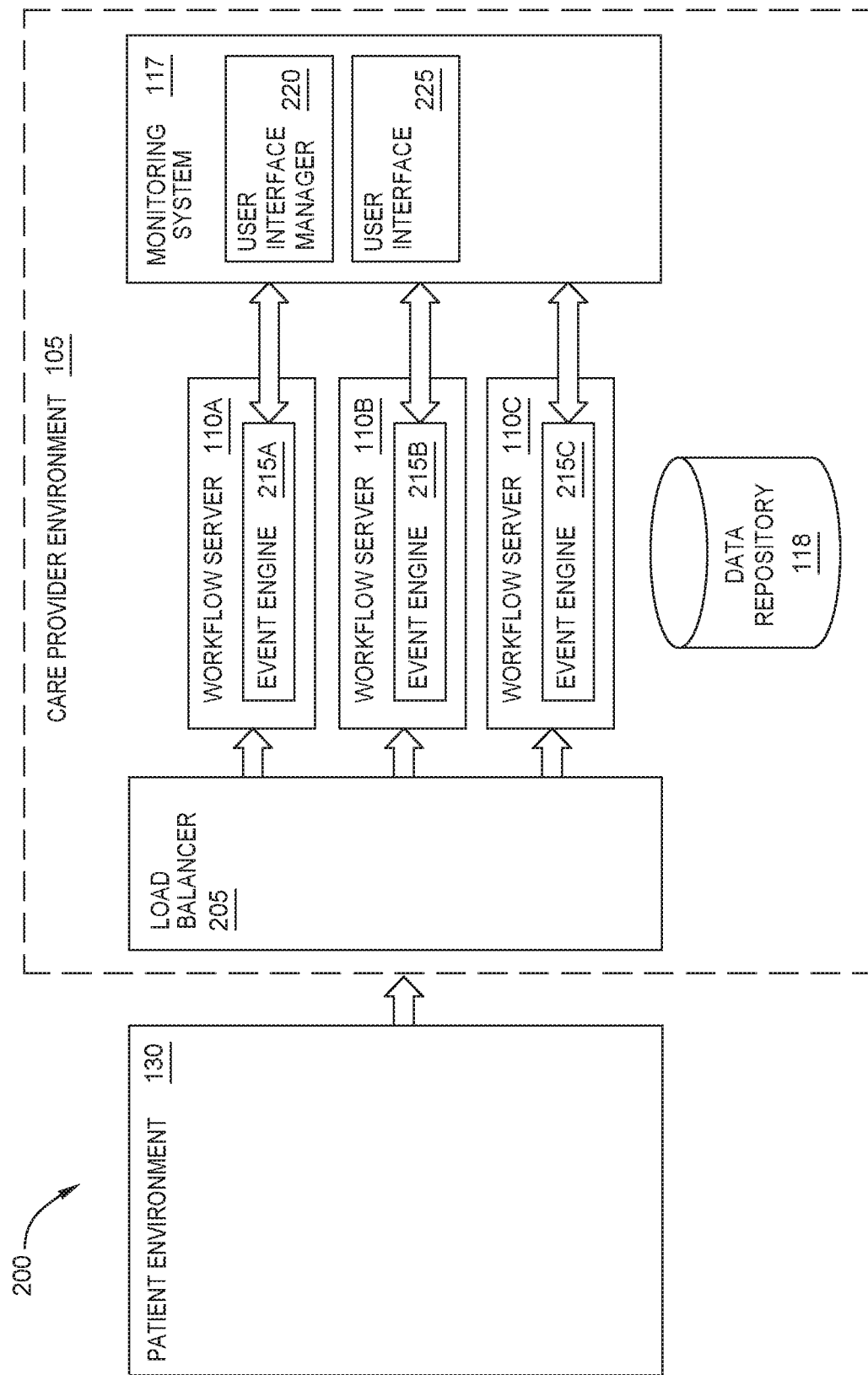
FIG. 2 illustrates a parallel processing computing environment, according to one embodiment.

FIG. 2 illustrates a parallel processing computing environment 200, according to one embodiment. As shown, the patient environment 130 transmits biometric data and/or health events to the care provider environment 105 which includes a load balancer 205. The workflow servers 110A-110C each include a respective one of the event engines 215A-215C. Although not shown, each of the event engines 215A-215C includes a plurality of interconnected processing nodes and queues that form a workflow for processing health events as discussed above. In one embodiment, the event engines 215A-215C each includes the same processing nodes and queues arranged in the same manner such that any one of the event engines 215A-215C can process the different health events generated by the at least one sensor device 140—i.e., any one of the event engines 215A-215C can process a cardiac event, respiratory event, maintenance event, etc. Based on current workload, the load balancer 205 transmits received data or heath events to one of the workflow servers 110A-110C for processing. For example, the load balancer 205 may assign the received health events in a round robin manner or by monitoring each respective central processing unit (CPU) or memory usage of the workflow servers 110A-110C.

Alternatively, the event engines 215A-215C may have different processing nodes and queues (or a different arrangement of the nodes and queues) such that the event engines 215A-215C are configured to process different event types. For example, the event engines 215A, 215B may have workflows that process cardiac events (and have the same processing nodes and queues), while the workflow in the event engine 215C processes respiratory events. The load balancer 205 may determine which of the event engines 215A-215C should receive the health event using the initial classification provided by the patient environment 130 or based on which of the at least one sensor device 140 measured the biometric data.

Regardless of whether the event engines 215A-215C have the same arrangement or different arrangements, compute resources can easily be adjusted in response to varying workloads. For example, if additional sensor devices (e.g., sensor devices 140) are added to the patient environment 130, a system administrator can add additional ones of the workflow servers 110A-110C to process an increased number of received health events. The reverse is also true. If the number of health events decreases, the administrator may remove one or more of the workflow servers 110A-110C. For example, if the event engines 215A, 215B both process cardiac events but the number of cardiac events has decreased, the system administrator may remove one of the workflow servers 110A, 110B. As another example, a load balancer component could monitor the usage of computational resources by the workflow servers 110A-110C and could scale the number of servers up or down, based on the computational resource usage.

With continued reference to FIG. 2, the monitoring system 117 includes a user interface manager 220 (UI manager) and a user interface 225 (UI). As discussed above, the processing nodes 114 may require input from the care provider 101 (FIG. 1) in order to route the health events through the event engines 215A-215C. To do so, the event engines 215A-215C transmit requests to the UI manager 220 which generates the UI 225 which can be displayed to the care provider 101. For example, the UI manager 220 may generate the UI 225 that includes an electrocardiogram (ECG) chart corresponding to a cardiac event. Further, the UI 225 may include I/O features (e.g., buttons or pull down menus) that the care provider can use to provide input or instructions to one of the event engines 215A-215C. For example, the care provider may instruct the one of the event engines 215A-215C to store the cardiac event in the data repository 118, send the cardiac event to one of the queues 115 (FIG. 1) that is monitored by another care provider (e.g., to get a second opinion), or forward the cardiac event to the care provider 101 of the patient 103. Thus, the monitoring system 117 permits the workflow servers 110 to output information to the care provider 101 as well as receive instructions from the care provider 101.

The event engines 215A-215C may store data in and retrieve data from the data repository 118. For example, the event engines 215 may maintain a patient history by storing all the received health events (or selected health events) derived based on monitoring a patient's vitals in the repository 118. Further, the event engines 215A-215C may use the data stored in the data repository 118 to process the health events. For example, if one of the event engines 215A-215C receives biometric data indicating the current weight of the patient 103, then the one of the event engines 215A-215C can retrieve past weight measurements for the patient 103 from the data repository 118 and derive a trend graph detailing how the weight of the patient 103 has changed over time. For instance, the patient's current weight may not be enough to trigger a health event, but the patient's derived weight change over a period of time may trigger a health event. As discussed below, these derived trends may be used to generate a derived observation (or other event(s)).

In one embodiment, the event engines 215A-215C prioritize health events, which, in turn, determines how quickly the health events are processed by the workflows in the event engines 215A-215C or what processing nodes and queues are used to process the health events. As discussed above, the health events may be prioritized based on a severity of the health event, the type of the health event, a characteristic of the patient 103 whose biometric data generated the health event, and the like. Additionally, the health events could be prioritized based on additional criteria, such as an institutional policy, a care plan-level policy, a patient-level policy, another policy or some combination of the above.

Figure 3:
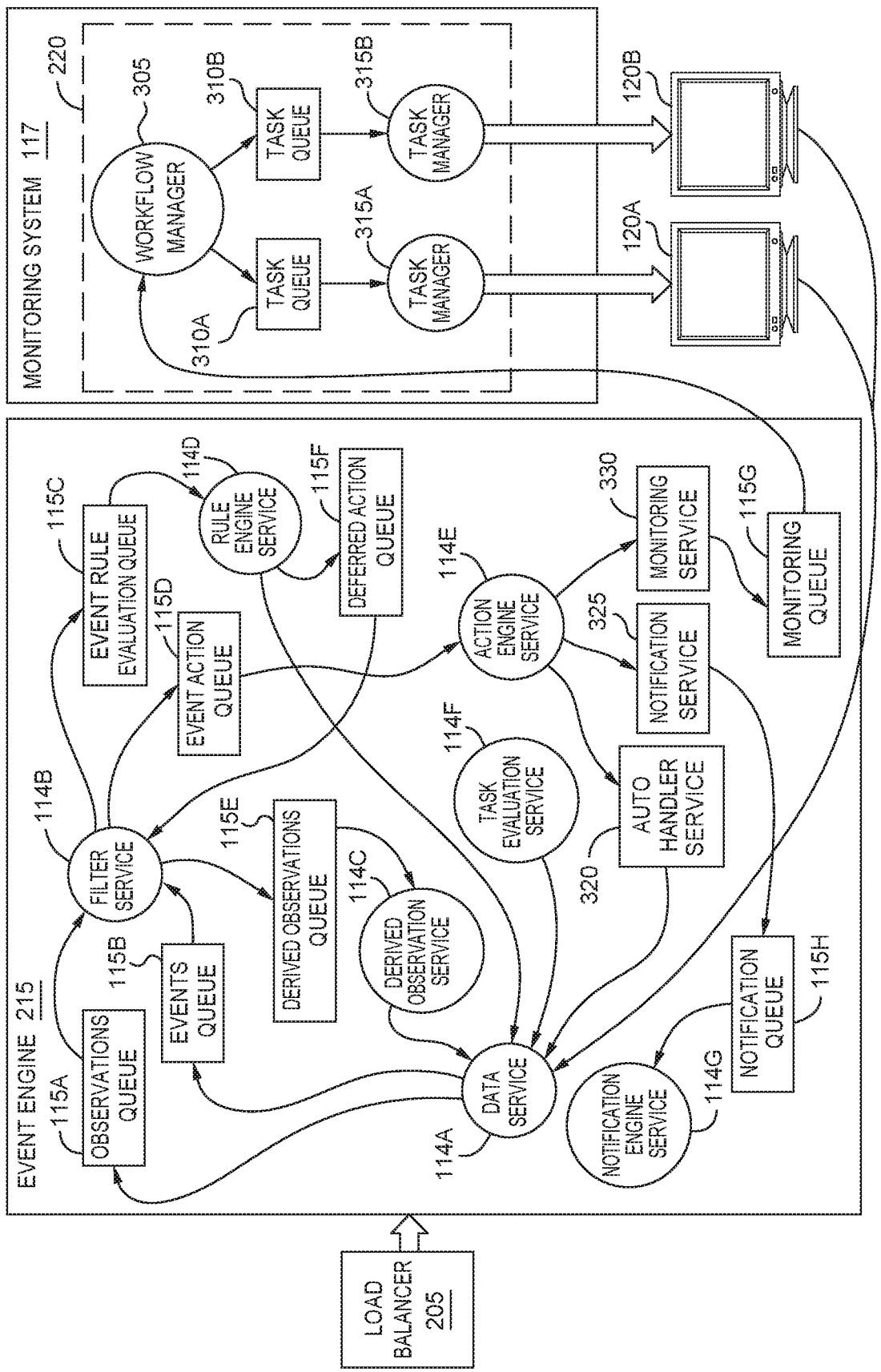
FIG. 3 illustrates an event engine for processing received health events, according to one embodiment.

FIG. 3 illustrates an event engine 215 that includes a workflow for processing health events, according to one embodiment. As described above, a health event or biometric data received from the sensors is forwarded from the load balancer 205 to the event engine 215. Specifically, a data service node 114A in the workflow receives the forwarded information from the load balancer 205. If the load balancer 205 forwards a health event, the data service node 114A classifies the health event based on type (e.g., a cardiac, respiratory, or maintenance event). In some cases, the health event was classified before being received by the data service node 114A. Nonetheless, the data service node 114A may review the data associated with the health event such as ECG data, breathing rate, blood pressure, etc. using more compute intensive techniques to determine whether the initial classification was correct. In another example, the data service node 114A may provide a more detailed classification of the health event than the initial classification. For example, the sensor device may have generated the health event because it detected an irregular heartbeat. However, the data service node 114A may evaluate the heartbeat and classify the health event as a specific cardiac health event—e.g., a ventricular trigeminy event or an atrioventricular block event. The data service node 114A may save the classification of the health event which is used by downstream nodes and queues to process the health event.

Instead of receiving a health event, the data service node 114A may receive raw data or observations from the patient environment. That is, the raw data or observations may not have been evaluated by a sensor device worn by the patient to determine if the data triggers a health event. For example, observation data from a sensor includes blood pressure measurements, weight measurements, ECG data, and the like. As discussed below, the event engine 215 evaluates these observations and can trigger health events which are then processed in the engine 215.

The data service node 114A forwards the observations to the observation queue 115A and the health events to the events queue 115B. A filter node 114B pulls the observations and health events stored in the queues 115A and 115B. This node 114B serves as a gatekeeper that determines where the health events and observations are routed for further processing. When evaluating observations, the filter node 114B may determine whether to ignore (i.e., drop) the observations or forward the observations to a derived observation queue 115E. For example, observations such as low battery signals, start signals indicating a sensor device has started collecting biometric data, or stop signals indicating a sensor device has stopped may be ignored by the filter service node 114B. In contrast, the node 114B may forward observations such as weight measurements, blood pressure measurements, ECG data, and the like to the derived observation queue 115E. In this manner, the filter service node 114B screens the incoming observations to determine whether they should be processed further such as checking for triggering health events.

Observations forwarded by the filter service node 114B are then processed by a derived observation service node 114C. This node 114C uses received observations in conjunction with previously received observations to create new observations or to generate a new health event. Stated differently, the derived observation service 114C may aggregate previously received observations with the currently received observations to compute statistics, trends, trigger health events, and the like. Although not shown, node 114C may be communicatively coupled to the data repository which stores past observations. For example, if the currently received observation is a weight measurement, the derived observation service node 114C may evaluate this measurement with previous weight measurements to determine a weight change for the patient over a defined period of time. This weight change may trigger a health event which is then forwarded to the data service node 114A for further processing. Even if a health event is not triggered, the derived observation service node 114C may store a derived observation (e.g., a weight change, average blood pressure, heart rate trends, etc.) in the data repository so that these data are available when further observations for the patient are received by the event engine 215 (or other event engines 215).

In one embodiment, health events may be processed by the derived observation service node 114C. For example, a sensor device may trigger a health event upon determining a patient's average blood pressure for a day exceeds a threshold. The filter service node 114B may forward this health event to the derived observation service node 114C which then may use past blood pressure measurements for that patient to derive a weekly or monthly average blood pressure for the patient, or a blood pressure trend graph. Based on this derived observation, the node 114C may generate a new health event or decide to drop the health event if the derived observation does not satisfy a corresponding condition.

Further, filter service node 114B also includes logic for determining whether received health events should be dropped, forwarded to an event action queue 115D, or forwarded to the event rule evaluation queue 115C. For example, a system administrator may determine that some health events are not relevant for certain patients. The logic in the filter service node 114B may identify and drop these health events to prevent them from propagating through the rest of the event engine 215. For instance, a patient may have a heart murmur that constantly results in a sensor device triggering a health event. Rather than continually processing these health events, a care provider can instruct the filter service node 114B to screen out (or suppress) these health events from the patient.

If a received health event has a corresponding action or actions, the filter service nodes 114B forward the health event to the event action queue 115D. However, if the action for a health event has not yet been identified, the filter service node 114B forwards the health event to the event rule evaluation queue 115C. A rule engine service node 114D pulls the health events from the queue 115C and evaluates the health event using one or more rules. Example rules include determining whether daily weight change and average blood pressure exceed respective thresholds. Based on this evaluation, the node 114D may determine what action the event engine 215 should perform—e.g., suppress/ignore the event, auto handle the event, display the event to a care provider, or delay processing the event. Once the action is determined, the rule engine service node 114D generates and forwards a new health event that includes the corresponding action to the data service node 114A. Now that the corresponding action is known, once the new health event reaches the filter service node 114B, it forwards the event to the event action queue 115D rather than the event rule evaluation queue 115D.

The rule engine service node 114D may delay processing the health event by forwarding the event to a deferred action queue 115F. The node 114D may do so when there is not enough available computing power to perform the rule evaluation or if the rule evaluation has not yet completed. That is, if all of the rules have not yet been evaluated and further evaluation is required before triggering the event action, then the event may be placed in queue 115F. For example, the rule may trigger a cardiac event but the system must first check to determine if that event is suppressed for the patient before taking the corresponding action. As shown, the health events stored in the deferred action queue 115F are then retrieved by the filter service node 114B and can be reintroduced into the event rule valuation queue 115C at a later time—i.e., when all the rules have been evaluated.

Once a corresponding action for a health event is known and the health event is stored in the event action queue 115D, an action engine service node 114E routes the health event to the appropriate action service—i.e., auto handler service 320, notification service 325, or monitoring service 330. The auto handler service 320 may perform actions that do not require supervision or input by a care provider—e.g., stores the health event in the data repository. As another example, the auto handler service 320 may assign a priority or severity to the health event before the event is reintroduced into the workflow with the new priority. The auto handler service 320 may also generate a new health event when, for example, a health event shows a cardiac event but the data quality is low. In response, the service 320 may introduce a maintenance event for checking the sensor connection/electrodes.

The event engine 215 uses notification service 325 to send information to the patient, a care giver, car provider, or device regarding the health event. The notification service 325 may include different communication channels or techniques for communicating with the patient such as email, chat, SMS messages, etc. Although FIG. 3 illustrates only one notification queue 115H and notification engine service node 114G for handling requests, the event engine 215 may have different queues and notification nodes for the different communication techniques. For example, if a maintenance event is triggered when an electrode is unplugged from a sensor device, the notification service 325 may transmit an email to the patient's mobile device instructing the patient to plug in the electrode. Alternatively, if a respiratory event is triggered because of an elevated breathing rate, the notification service may send an SMS message to the patient asking her if she is currently performing a physical activity.

The monitoring service 330 communicatively couples the event engine 215 to the monitoring system 117. When input from a care provider regarding a health event is desired, the monitoring service 330 forwards the health event to a monitoring queue 115G. The UI manager 220 in the monitoring system 117 includes a workflow manager node 305 that pulls health events from the monitoring queue 115G and assigns them to either task queue 310A or 310B. The UI manager 220 also includes task manager nodes 315A and 315B which generate UIs for the health events. These UIs are then displayed to care providers via the computing devices 120A and 120B. Further, the task manager nodes 315 may place the biometric or maintenance data associated with the health events in the UIs. For example, a UI for a cardiac event may display an ECG graph and a baseline chart, while a UI for respiratory event displays a breathing rate and oxygen levels in the blood. In this manner, the UI manager 220 can generate a customized UI for the different health events.

The computing devices 120 may transmit information to the data service node 114A of the event engine 215 which can be used to generate new health events or update current health events. For example, the care provider may instruct the event engine 215 to take a certain action such as forwarding the health event to a different care provider to get a second opinion, reclassifying the health event, suppressing or ignoring the health event, notifying a health care provider, and the like. Based on the care provider's input, the event engine 215 again routes the health event through the nodes 114 and queues 115.

The event engine 215 also includes a task evaluation service node 114F. Unlike the other nodes and queues in event engine 215 which process or store observation data or health events received from the patient environment, the task evaluation service node 114F determines whether to trigger a health event based on a care protocol or care plan. In one embodiment, the node 114F triggers a health event when the patient does not follow the care protocol or plan. For example, the care protocol may ask that the patient wear a sensor device for a certain amount of time during the day or take weight measurements each day. By monitoring the observation and health events received by the event engine 215, the task evaluation service node 114F determines whether the patient has complied with the care protocol. If not, the task evaluation service node 114F triggers a health event with a corresponding action for the event engine 215 to perform such as sending a notification to the patient using notification service 325 or informing a care provider using the monitoring service 330.

Figure 4A:
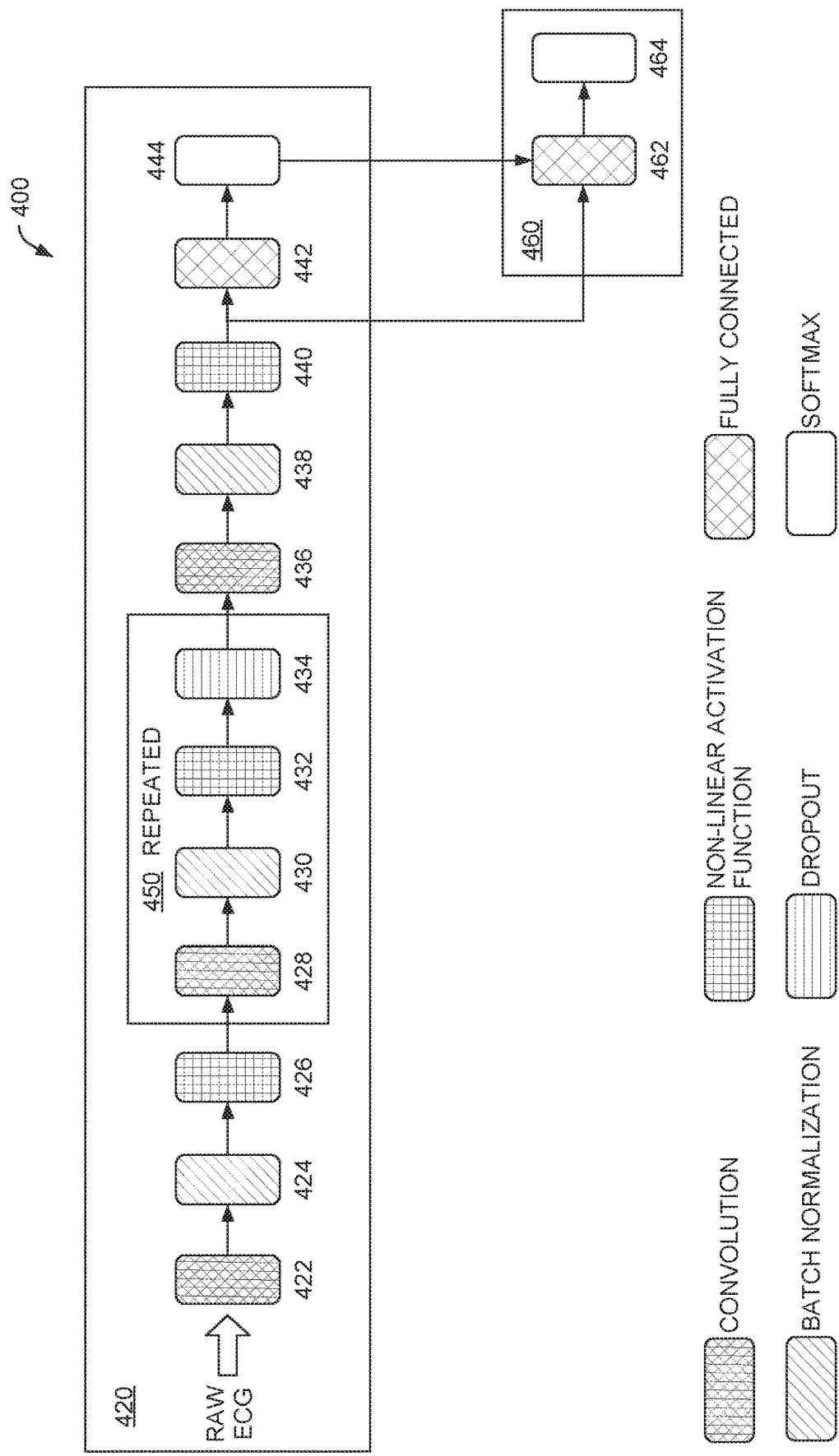
FIGS. 4A-B illustrate a deep learning architecture for identifying main rhythms and "with rhythms" from ECG data, according to one embodiment.
Figure 4B:
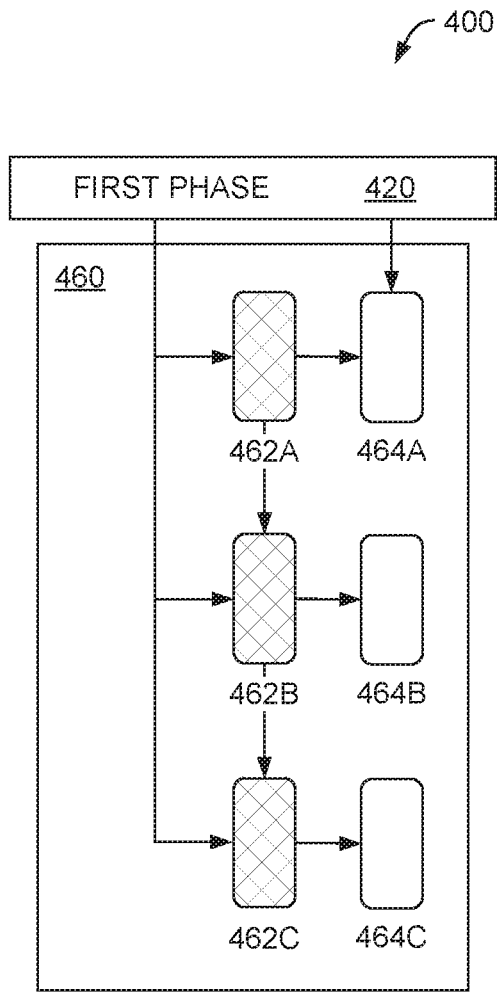

FIGS. 4A-B illustrate a deep learning architecture for identifying main rhythms and "with rhythms" from ECG data, according to one embodiment. The deep learning architecture 400 is a machine learning architecture, and includes two phases. In the first phase 420, the raw ECG data are used to classify a main rhythm. For example, as illustrated in FIG. 4A, raw ECG data can be provided to a convolutional layer 422 connected with a batch normalization layer 424 and a non-linear activation function 426 (e.g., a rectified linear unit (ReLU)). The output from that combination can be provided to a convolution layer 428, connected with a batch normalization layer 430, a non-linear activation function 432, and a dropout layer 434. In an embodiment, a non-linear activation function is merely one example. Any suitable activation function layer can be used. Further, in an embodiment, a dropout layer is merely one example. Any suitable regularization layer can be used. In an embodiment, the convolution layer 428, batch normalization layer 430, non-linear activation function 432, and dropout layer 434 form a combination 450. This combination can be repeated, as appropriate. The output from the dropout layer 434 is then provided to a convolutional layer 436 connected with a batch normalization layer 438 and a non-linear activation function 440. The output from this final non-linear activation function 440 is provided to a fully connected layer 442, which is connected with a softmax layer 444.

In an embodiment, the phase 420 uses this configuration of layers to classify a main rhythm from raw ECG data. The specific configuration of layers illustrated in the phase 420 is merely an example, and other suitable configurations could be used (e.g., with more layers, fewer layers, or different layers). Further, the example illustrated in FIG. 4A uses a convolutional neural network, but other suitable deep learning or machine learning techniques could be used. The phase 420 can also be used to identify noise.

Further, in an embodiment, convolutional layers 422 through 440 are designed such that they compress the raw ECG data into a feature set (e.g., a feature vector) that incrementally spans small segments of time (e.g., 0.1 seconds, 0.2 seconds, 0.5 seconds, or 1 second). The segment of time can depend on the classification task. The fully connected layer 442 and the softmax layer 444 operate on the feature set generated by the convolutional layers to perform a classification task.

The deep learning architecture 400 includes a second phase 460. In an embodiment, the second phase 460 is used to identify the "with rhythm" occurring in parallel with the main rhythm identified in the first phase 420. For example, as illustrated in FIG. 4, the second phase 460 includes a fully connected layer 462 and a softmax layer 464. The fully connected layer 462 receives as input both the feature vector output by the non-linear activation function 440 and the classified main rhythm output by the softmax layer 444. In an embodiment, the second phase 460 can be trained using supervised learning to make a binary determination as to whether a particular pre-determined type of "with rhythm" is present. The fully connected layer 462 and the softmax layer 464 are merely examples. Other suitable machine learning techniques could also be used.

Further, as illustrated in FIG. 4B, the second phase 460 can include multiple classifiers and multiple phases (e.g., multiple combinations of a fully connected layer 462A-C and a softmax layer 464A-C). Each of these classifiers can be used to classify a different "with rhythm." For example, the second phase 460 can include a first fully connected layer 462A and a first softmax layer 464A to detect intraventricular conduction delay (IVCD). The second phase, or a third phase, can further include a second fully connected layer 462B and a second softmax layer 464B to detect first degree heart block. The second phase, or a fourth phase, can further include a third fully connected layer 462C and a third softmax layer 464C to detect another "with rhythm." In an embodiment, each of these fully connected layers 462A-C receives as input the feature vector and the classification output by the first phase 420. Further, in an embodiment, each of these "with rhythm" classifiers can operate in parallel, to identify multiple different possible "with rhythms" based on the output from the first phase 420.

Figure 5:
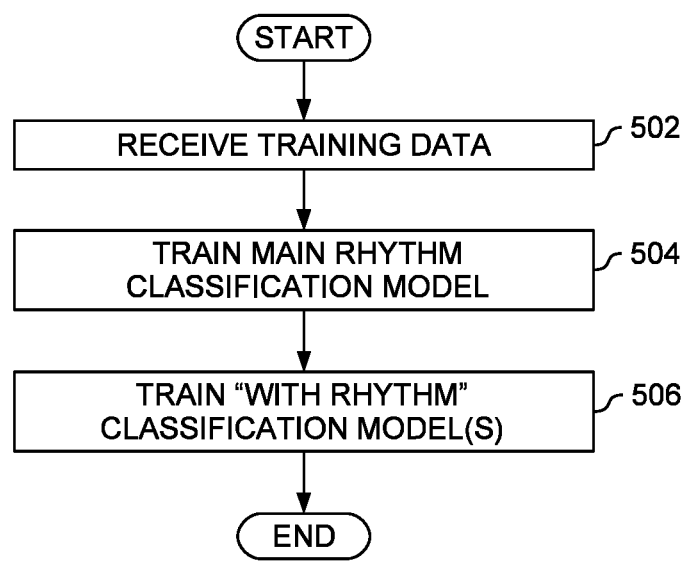
FIG. 5 is a flowchart for training a deep learning architecture for identifying main rhythms and "with rhythms" from ECG data, according to one embodiment.

FIG. 5 is a flowchart for training a deep learning architecture for identifying main rhythms and "with rhythms" from ECG data, according to one embodiment. At block 502, training data are received. In an embodiment, supervised learning techniques are used and the training data includes sample ECG data labeled with appropriate classifications. At block 504, the main rhythm classification model (e.g., the first phase 420 illustrated in FIG. 4A) is trained using the training data. In an embodiment, the training data includes ECG data labeled with main rhythm classifications, and this training data are used to train the main rhythm classification model. At block 506, the "with rhythm" classification model(s) (e.g., the second phase 460 illustrated in FIGS. 4A-B) are trained using training data. In an embodiment, the training data used at block 506 includes the output from the block 504, labeled accurately, including both a feature vector generated from ECG training data and the corresponding classification.

In the embodiment illustrated in FIG. 5, the main rhythm classification model is trained before the "with rhythm" classification model. Alternatively, these models could be trained together. For example, these models could be trained simultaneously by merging (e.g., through weighted averaging or another suitable technique) the loss functions calculated from the outputs of each softmax layer. In this example, segments of ECG data could be provided with multiple labels (e.g., a main rhythm classification and a "with rhythm" classification), and the model could provide multiple corresponding classifications (e.g., the main rhythm classification and the "with rhythm" classification). A weighted loss function can be used to facilitate training by determining which result classification should be weighted more. In this embodiment, the deep learning model could have the structure illustrated in FIGS. 4A-4B. Alternatively, the connection between the first phase softmax 444 and the second phase fully connected 462 could be removed.

Training the models together could result in improved classification performance, in some circumstances, because the convolutional layers have more opportunity to produce features that are more relevant to the "with rhythm" classifications. But this training may also require more configuration, including careful tuning of the loss function in order to focus the deep learning model's priority on main rhythm classification, which in most circumstances should take priority over correct "with rhythm" classification. Further, this training could require more data, which may be difficult or expensive to acquire.

Figure 6:
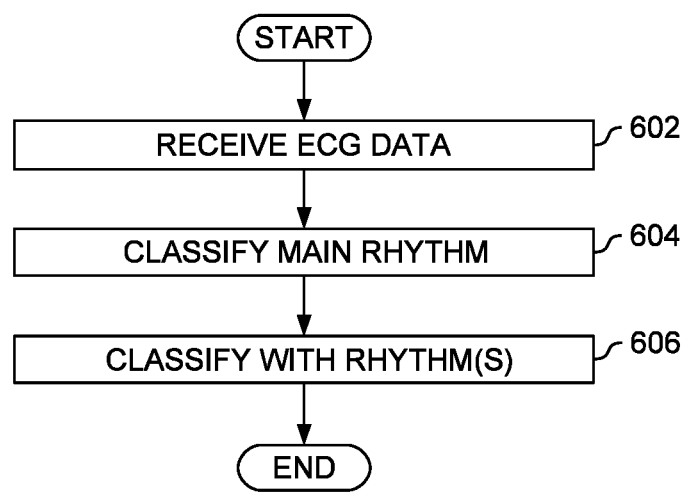
FIG. 6 is a flowchart for classifying main rhythms and "with rhythms" using a deep learning architecture, according to one embodiment.

FIG. 6 is a flowchart for classifying main rhythms and "with rhythms" using a deep learning architecture, according to one embodiment. At block 602, ECG data are received. In an embodiment, this includes raw ECG data from a patient. Alternatively, this ECG data can be pre-processed in a suitable fashion (e.g., to provide gain or attenuation for desired aspects of the ECG data). At block 604, the ECG data are fed to a deep learning architecture (e.g., the first phase 420 illustrated in FIG. 4A), which classifies the main rhythms in the ECG data. As discussed above, in an embodiment the deep learning architecture can classify the data in small segments of time. These segments of time can depend on the classification task. At block 606, the output from block 604 (including, e.g., the generated feature vector and classifications) is fed to a deep learning architecture (e.g., the second phase 460 illustrated in FIGS. 4A-B) which classifies "with rhythms" in the data. As discussed above, the deep learning architecture can be designed to classify multiple "with rhythms", in parallel.

Figure 7:
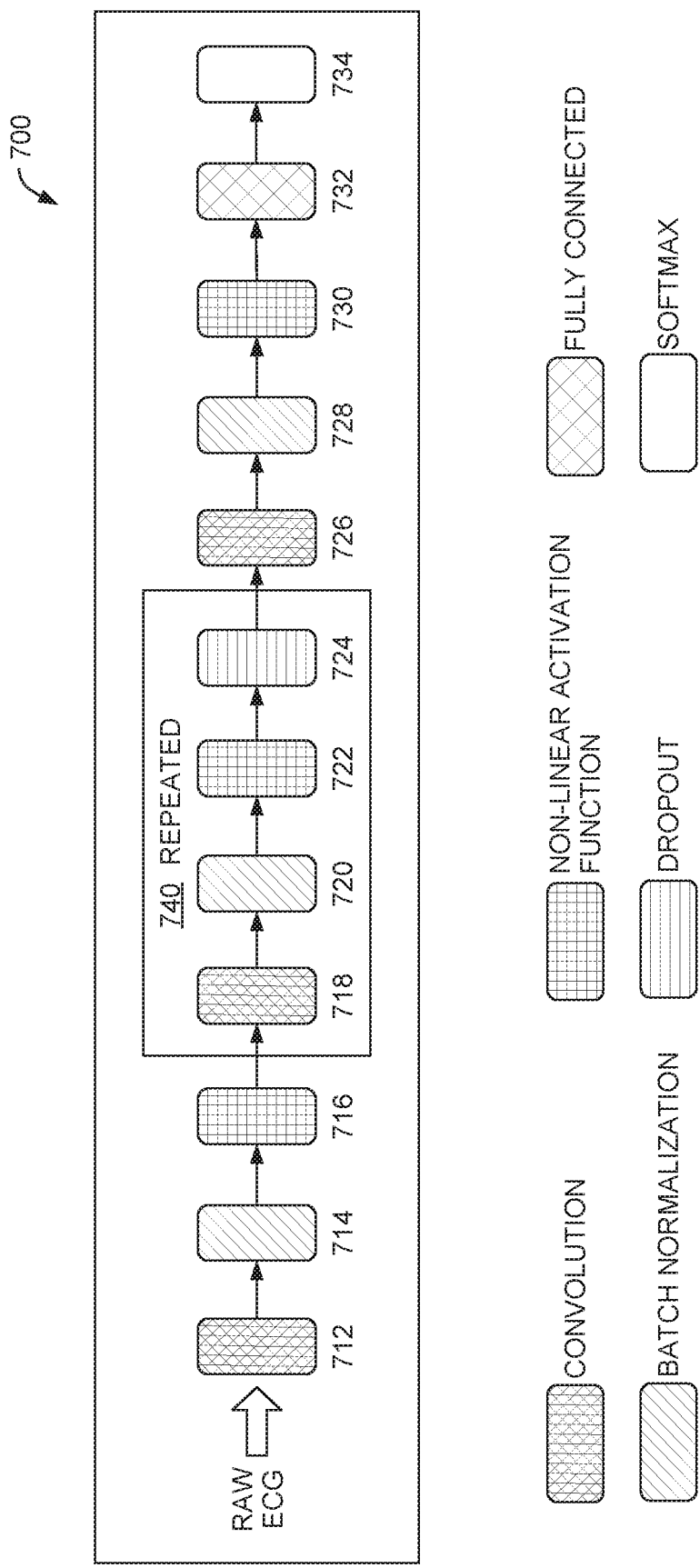
FIG. 7 illustrates a deep learning architecture for classifying cardiac events using single channel ECG data, according to one embodiment.

FIG. 7 illustrates a deep learning architecture for classifying cardiac events using single channel ECG data, according to one embodiment. The deep learning architecture 700 can be used to classify raw ECG data to identify specific beats or rhythms. This is merely an example architecture, and other suitable configurations can be used. As illustrated in FIG. 7, raw ECG data can be provided to a convolutional layer 712 connected with a batch normalization layer 714 and a non-linear unit 716 (e.g., a ReLU). The output from that combination can be provided to a convolution layer 718, connected with a batch normalization layer 720, a non-linear activation function 722, and a dropout layer 724. In an embodiment, the convolution layer 718, batch normalization layer 720, non-linear activation function 722, and dropout layer 724 form a combination 740. This combination can be repeated, as appropriate. The output from the dropout layer 724 is then provided to a convolutional layer 726 connected with a batch normalization layer 728 and a non-linear activation function 730. The output from this final non-linear activation function 730 is provided to a fully connected layer 732, which is connected with a softmax layer 734. The deep learning architecture 700 takes as input raw ECG data and classifies these data to identify particular cardiac events.

As illustrated in FIG. 7, the deep learning architecture for classifying a single channel beat or rhythm is a convolutional neural network. As discussed above, this configuration is merely an example, and other suitable configurations can be used (e.g., with more, fewer, or different layers and connections). Further, other common deep learning architectures can be used. For example, a recurrent neural network, or any other suitable deep learning architecture, can be used.

Figure 8:
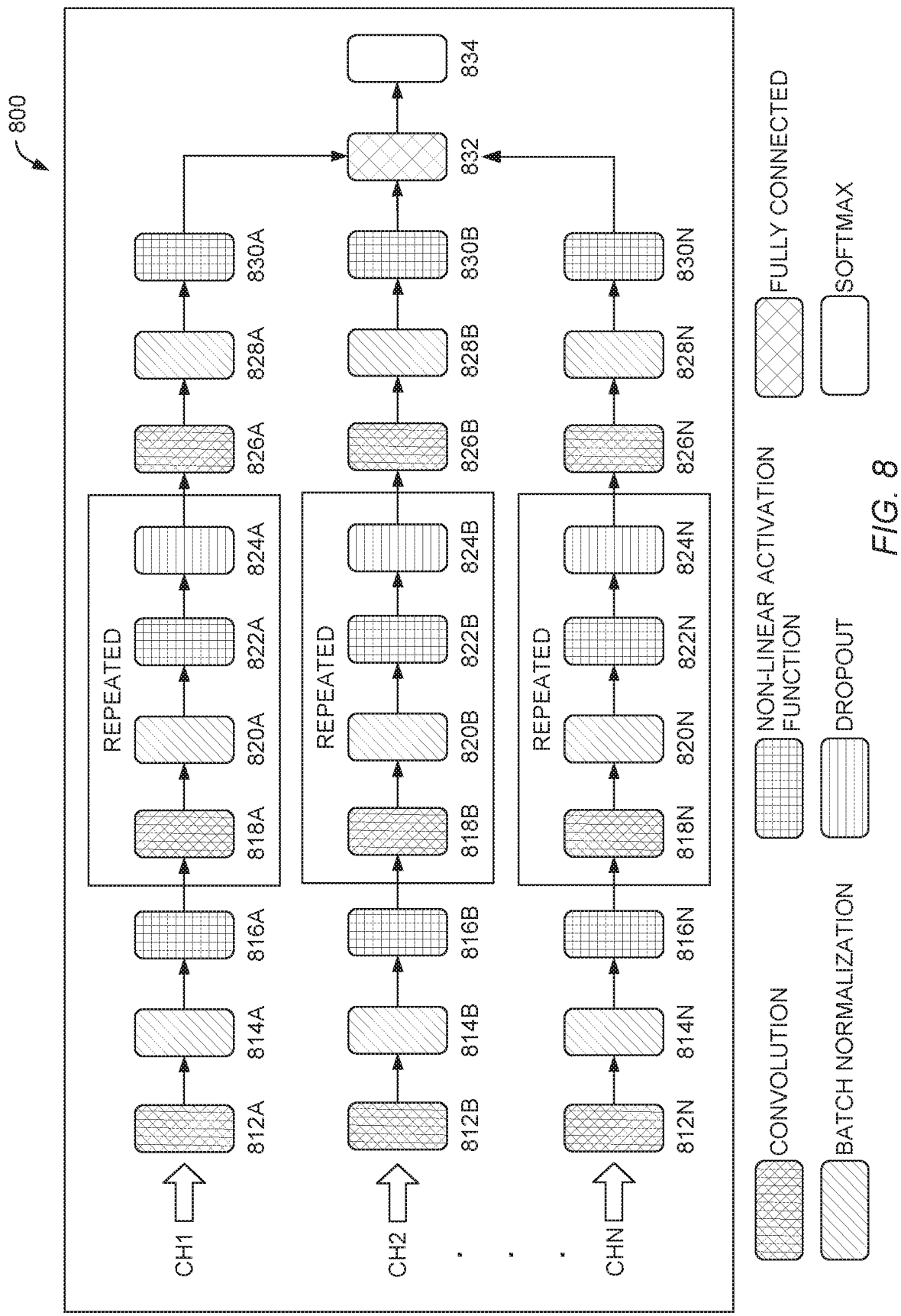
FIG. 8 illustrates a deep learning architecture for classifying cardiac events using multi-channel ECG data.

FIG. 8 illustrates a deep learning architecture for classifying cardiac events using multi-channel ECG data. In an embodiment, the deep learning architecture illustrated in FIG. 7 can be modified to classify multiple channels of ECG data. As discussed above, a patient can wear a cardiac monitoring device that detects multiple channels of ECG data. The deep learning architecture 800, illustrated in FIG. 8, leverages an existing single channel architecture (e.g., the architecture 700 illustrated in FIG. 7) to classify beats and rhythms based on multiple channels of ECG data. In an embodiment, this is done by removing the final classification layers from the existing, fully-trained architecture (e.g., the fully connected layer 732 and the softmax 734). This produces a feature extraction network, which generates a feature vector. Each channel of data is analyzed to produce its own feature vector, and the feature vectors are passed to a new set of classification layers (e.g., the fully connected layer 832 and the softmax layer 834) that have been trained using the concatenated features generated from each layer. While FIG. 8 uses a fully connected layer 832 and a softmax layer 834, as an example classification layer, other suitable machine learning structures and techniques (e.g., more, fewer, or different layers and connections) can be used.

As illustrated in FIG. 8, one channel of ECG data is provided to the feature classification portion of an existing single channel deep learning beat or rhythm classifier. For example, channel 1 ECG data can be provided to a convolutional layer 812A connected with a batch normalization layer 814A and a non-linear unit 816A (e.g., a ReLU). The output from that combination can be provided to a convolution layer 818A, connected with a batch normalization layer 820A, a non-linear activation function 822A, and a dropout layer 824A. In an embodiment, the convolution layer 818A, batch normalization layer 820A, non-linear activation function 822A, and dropout layer 824A form a combination that can be repeated, as appropriate. The output from the dropout layer 824A is then provided to a convolutional layer 826A connected with a batch normalization layer 828A and a non-linear activation function 830A.

Channel 2 ECG data can be provided to a convolutional layer 812B connected with a batch normalization layer 814B and a non-linear activation function 816B (e.g., a ReLU). The output from that combination can be provided to a convolution layer 818B, connected with a batch normalization layer 820B, a non-linear activation function 822B, and a dropout layer 824B. In an embodiment, the convolution layer 818B, batch normalization layer 820B, non-linear activation function 822B, and dropout layer 824B form a combination that can be repeated, as appropriate. The output from the dropout layer 824B is then provided to a convolutional layer 826B connected with a batch normalization layer 828B and a non-linear activation function 830B.

This can be repeated for as many channels as are included in the ECG data, up to channel N. Channel N ECG data can be provided to a convolutional layer 812N connected with a batch normalization layer 814N and a non-linear activation function 816N (e.g., a ReLU). The output from that combination can be provided to a convolution layer 818N, connected with a batch normalization layer 820N, a linear unit 822N, and a dropout layer 824N. In an embodiment, the convolution layer 818N, batch normalization layer 820N, non-linear activation function 822N, and dropout layer 824N form a combination that can be repeated, as appropriate. The output from the dropout layer 824N is then provided to a convolutional layer 826N connected with a batch normalization layer 828N and a non-linear activation function 830N.

In an embodiment, convolutional layers 812A-N through 830A-N are designed such that they compress the ECG channel data into a feature set (e.g., a feature vector) that incrementally spans small segments of time (e.g., 0.1 seconds, 0.2 seconds, 0.5 seconds, or 1 second). The feature vectors are provided to a combined classifier layer, for example the fully connected layer 832 and the softmax 834. The output of the softmax 834 is a classification of cardiac events, based on analyzing the ECG channel data.

In an embodiment, the architecture illustrated in FIG. 8 can have numerous advantages. For example, using multiple channels of ECG data can enhance the accuracy of classification, by weighing information in channels that measure electrical propagation in different directions relative to the heart. As another example, using multiple channels of ECG data can provide redundancy that allows for the ECG to be interpreted when one or more channels have low signal to noise ratio due to noise caused by movement, muscle activity, or issues with the tissue electrode interface.

Figure 9:
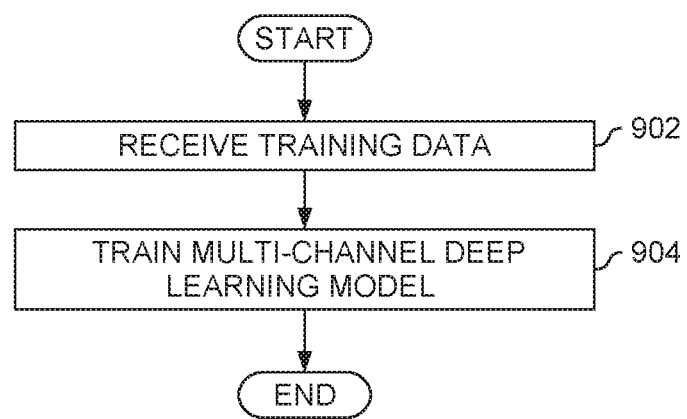
FIG. 9 is a flowchart for training a deep learning architecture for classifying cardiac events using multi-channel ECG data, according to one embodiment.

FIG. 9 is a flowchart for training a deep learning architecture for classifying cardiac events using multi-channel ECG data, according to one embodiment. At block 902, training data are received, and at block 904 the training data are used to train the deep learning model (e.g., the architecture 800 illustrated in FIG. 8). In an embodiment, the architecture illustrated in FIG. 8 improves and simplifies training of the deep learning architectures.

For example, a single channel classifier (e.g., the deep learning architecture 700 illustrated in FIG. 7) can be trained on a labeled data set of single channel data to classify cardiac events. This existing classifier can then be leveraged to classify multi-channel data, without requiring a specific multi-channel data set of training data. Multiple single channel ECG training data strips can be fed into multiple channel paths (e.g., 812A-830A, 812B-830B, and 812N-830N illustrated in FIG. 8), each path creating a feature vector. The feature vectors can then be fed into the classifier layers (e.g., the fully connected layer 832 and the softmax 834). Instead of requiring separate training data for each possible grouping of channels (e.g., separate 3 channel training data, separate 12 channel training data, separate 64 channel training data, etc.), the deep learning architecture 800 can be trained using existing single channel training data. Rather than requiring hundreds of thousands (or millions) of pieces of training data, the multichannel extension of the single channel deep learning architecture 800 can be accurately trained with only hundreds or thousands of training examples. This is possible because the classifier layers (e.g., the fully connected layer 832 and the softmax 834) have many fewer parameters when classifying the cardiac events based on the multi-channel data.

Figure 10:
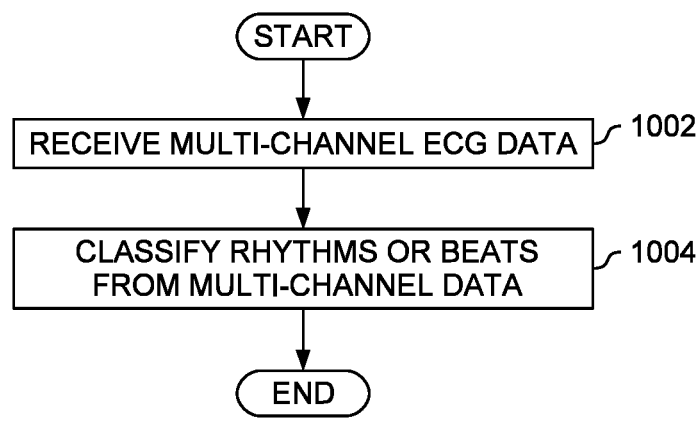
FIG. 10 is a flowchart for classifying cardiac events using multi-channel ECG data and a deep learning architecture, according to one embodiment.

FIG. 10 is a flowchart for classifying cardiac events using multi-channel ECG data and a deep learning architecture, according to one embodiment. At block 1002 multi-channel ECG data are received, and at block 1004 these data are classified to identify the desired rhythms or beats, using a deep learning model (e.g., the deep learning architecture 800 illustrated in FIG. 8). In an embodiment, as discussed above, single channel classifiers are leveraged to determine a feature vector for each channel of data, and the feature vectors are fed into a combined classifier layer (e.g., the fully connected layer 832 and the softmax 834) to classify the cardiac events.

The classified data (e.g., as described in relation to FIGS. 4A-B and FIG. 8) are used to inform and treat the patient. For example, the machine learning architectures can identify cardiac irregularities. Devices in the computing environment (e.g., the computing environment 100 illustrated in FIG. 1) can then be used to treat the cardiac irregularity in the patient. For example, a particular medical treatment (e.g., a medication or a patient behavior) for the cardiac irregularity identified using the machine learning architecture could be recommended to the patient using the patient's mobile device (e.g., the mobile device 135 illustrated in FIG. 1). As another example, a report could be generated for a physician treating the patient, using the classified data. Alternatively, a report could be generated for the patient him- or herself. Further, a patient care plan could be generated or modified based on the classification. For example, a patient care plan for a patient could be generated based on the classification. The patient care plan could provide medical treatment options (e.g., medication, educational content, behavioral changes, etc.) for the patient based on the classification. Further, an existing care plan for the patient could be modified.

In addition, an alert or output could be generated for the patient, care provider, or other interested parties. For example, an alert could be provided to the patient using a graphical user interface on a device operated by the patient (e.g., a mobile device 135 as illustrated in FIG. 1 or computer). Alternatively, an alert could be provided to the patient's care provider using a graphical user interface on a device operated by the care provider (e.g., a mobile device or a computing device 120 as illustrated in FIG. 1).

The deep learning models discussed above can operate in a variety of locations. For example, a deep learning model can operate as part of the care provider environment 105 (e.g., on workflow server 110, computing device 120, or monitoring system 117). The model can operate on a dedicated computing system or a virtual computer instance (e.g., a cloud computing platform). Further, the deep learning model can operate on a device in the patient environment 130, including mobile device 135 and sensor devices 140. The deep learning model can be computationally intensive, however, and so the mobile device 135 or sensor devices 140 (or any of the devices in care provider environment 105) can include specialized hardware for training and running the deep learning model. To facilitate classification, the input and output of the deep learning model can be stored in a suitable location (e.g., the data repository 118 illustrated in FIG. 1).

In the preceding, reference is made to embodiments presented in this disclosure. However, the scope of the present disclosure is not limited to specific described embodiments. Instead, any combination of the described features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s).

As will be appreciated by one skilled in the art, the embodiments disclosed herein may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium is any tangible medium that can contain, or store a program for use by or in connection with an instruction execution system, apparatus or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described below with reference to flowchart illustrations and/or block diagrams of methods, apparatus (systems) and computer program products according to embodiments presented in this disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

We claim:

1. A computer-implemented method for classifying cardiac events, comprising:

generating a feature set by analyzing electrocardiogram (ECG) data for a patient using a first phase in a machine learning architecture comprising a convolutional neural network;

classifying, based on the feature set and using the first phase in the machine learning architecture, a first cardiac event in the ECG data, the first cardiac event comprising a first cardiac event type, wherein the feature set is generated prior to the classifying of the first cardiac event;

determining, based on the classified first cardiac event, a binary classification indicating whether the ECG data contain a predetermined second cardiac event, the second cardiac event comprising a second cardiac event type different from the first cardiac event type, comprising:

providing the classified first cardiac event as input to a second phase in the machine learning architecture, comprising providing an output of a softmax layer in the first phase as input to a fully connected layer in the second phase;

providing the feature set generated by the first phase as input to the second phase, comprising providing an output of a non-linear activation function layer in the first phase as input to the fully connected layer in the second phase;

outputting, by the softmax layer in the second phase, the binary classification; and determining, based on the classified first cardiac event, a third, binary classification indicating whether the ECG data contain a predetermined third cardiac event, the third cardiac event comprising a third cardiac event type different from the first and second cardiac event types, comprising:

providing the classified first cardiac event as input to a third phase in the machine learning architecture, comprising providing the output of the softmax layer in the first phase as input to a fully connected layer in the third phase;

providing the feature set generated by the first phase as input to the third phase, comprising providing the output of the non-linear activation function layer in the first phase as input to the fully connected layer in the third phase;

providing an output of the fully connected layer in the third phase to a softmax layer in the third phase; and outputting, by the softmax layer in the third phase, the third, binary classification;

wherein the second and third phases are trained to use transfer learning between the classifying the first cardiac event type in the first phase and the classifying the second and third cardiac event types in the second and third phases to classify the second and third cardiac events, wherein the second and third cardiac events occur at least partially at the same time as the first cardiac event, and wherein the classified first cardiac event and the classified second cardiac event are configured to be used in medical treatment of the patient.

2. The computer-implemented method of claim 1, wherein the convolutional neural network comprising the first phase in the machine learning architecture comprises a set of connected layers comprising:

a convolution layer;
a batch normalization layer;
an activation function layer; and
a regularization layer.

3. The computer-implemented method of claim 2, wherein the regularization layer comprises a dropout layer.

4. The computer-implemented method of claim 1, wherein the second phase of the machine learning architecture is trained based on the first phase of the machine learning architecture.

5. The computer-implemented method of claim 1, wherein the second phase of the machine learning architecture is trained at the same time as the first phase of the machine learning architecture.

6. The method of claim 1, further comprising:

receiving the ECG data for the patient at a server in a care provider environment, wherein the ECG data are collected from the patient and transmitted to the server using one or more remote monitoring devices.

7. The method of claim 6, wherein the one or more remote monitoring devices comprise a sensor device and a mobile device, and wherein the ECG data are collected using the sensor device and transmitted to the server using the mobile device.

8. The method of claim 1, further comprising:

classifying a fourth cardiac event, comprising a fourth cardiac event type different from the first and second and third cardiac event types, in the ECG data based on the classified first cardiac event, comprising:

providing the classified first cardiac event, and the feature set generated by the first phase, as input to a fourth phase in the machine learning architecture, wherein the fourth phase is trained to use transfer learning between the classifying the first cardiac event type in the first phase and the classifying the fourth cardiac event type in the fourth phase to classify the fourth cardiac event, wherein the fourth cardiac event occurs at least partially at the same time as the first cardiac event, and wherein the classifying the fourth cardiac event and the classifying the second and third cardiac events occur at least partially in parallel.

9. A system, comprising:

a processor; and a memory storing a program, which, when executed on the processor, performs an operation, the operation comprising:

generating a feature set by analyzing electrocardiogram (ECG) data for a patient using a first phase in a machine learning architecture comprising a convolutional neural network;

classifying, based on the feature set and using the first phase in the machine learning architecture, a first cardiac event in the ECG data, the first cardiac event comprising a first cardiac event type wherein the feature set is generated prior to the classifying of the first cardiac event;

determining, based on the classified first cardiac event, a binary classification indicating whether the ECG data contain a predetermined second cardiac event, the second cardiac event comprising a second cardiac event type different from the first cardiac event type, comprising:

providing the classified first cardiac event as input to a second phase in the machine learning architecture, comprising providing an output of a softmax layer in the first phase as input to a fully connected layer in the second phase;

providing the feature set generated by the first phase as input to the second phase, comprising providing an output of a non-linear activation function layer in the first phase as input to the fully connected layer in the second phase;

outputting, by the softmax layer in the second phase, the binary classification; and determining, based on the classified first cardiac event, a third, binary classification indicating whether the ECG data contain a predetermined third cardiac event, the third cardiac event comprising a third cardiac event type different from the first and second cardiac event types, comprising:

providing the classified first cardiac event as input to a third phase in the machine learning architecture, comprising providing the output of the softmax layer in the first phase as input to a fully connected layer in the third phase;

providing the feature set generated by the first phase as input to the third phase, comprising providing the output of the non-linear activation function layer in the first phase as input to the fully connected layer in the third phase;

providing an output of the fully connected layer in the third phase to a softmax layer in the third phase; and outputting, by the softmax layer in the third phase, the third, binary classification;

wherein the second and third phases are trained to use transfer learning between the classifying the first cardiac event type in the first phase and the classifying the second and third cardiac event types in the second and third phases to classify the second and third cardiac events, wherein the second and third cardiac events occur at least partially at the same time as the first cardiac event, and wherein the classified first cardiac event and the classified second cardiac event are configured to be used in medical treatment of the patient.

10. The system of claim 9, the operation further comprising:

classifying a fourth cardiac event, comprising a fourth cardiac event type different from the first and second and third cardiac event types, in the ECG data based on the classified first cardiac event, comprising:

providing the classified first cardiac event, and the feature set generated by the first phase, as input to a fourth phase in the machine learning architecture, wherein the fourth phase is trained to use transfer learning between the classifying the first cardiac event type in the first phase and the classifying the fourth cardiac event type in the fourth phase to classify the fourth cardiac event, wherein the fourth cardiac event occurs at least partially at the same time as the first cardiac event, and wherein the classifying the fourth cardiac event and the classifying the second and third cardiac events occur at least partially in parallel.

11. The system of claim 9, wherein the second phase of the machine learning architecture is trained based on the first phase of the machine learning architecture.

12. The system of claim 9, wherein the second phase of the machine learning architecture is trained at the same time as the first phase of the machine learning architecture.

13. A non-transitory computer-readable medium containing computer program code that, when executed using one or more computer processors, performs an operation, the operation comprising:

generating a feature set by analyzing electrocardiogram (ECG) data for a patient using a first phase in a machine learning architecture comprising a convolutional neural network;

classifying, based on the feature set and using the first phase in the machine learning architecture, a first cardiac event in the ECG data, the first cardiac event comprising a first cardiac event type, wherein the feature set is generated prior to the classifying of the first cardiac event;

determining, based on the classified first cardiac event, a binary classification indicating whether the ECG data contain a predetermined second cardiac event, the second cardiac event comprising a second cardiac event type different from the first cardiac event type, comprising:

providing the classified first cardiac event as input to a second phase in the machine learning architecture, comprising providing an output of a softmax layer in the first phase as input to a fully connected layer in the second phase;

providing the feature set generated by the first phase as input to the second phase, comprising providing an output of a non-linear activation function layer in the first phase as input to the fully connected layer in the second phase;

outputting, by the softmax layer in the second phase, the binary classification; and determining, based on the classified first cardiac event, a third, binary classification indicating whether the ECG data contain a predetermined third cardiac event, the third cardiac event comprising a third cardiac event type different from the first and second cardiac event types, comprising:

providing the classified first cardiac event as input to a third phase in the machine learning architecture, comprising providing the output of the softmax layer in the first phase as input to a fully connected layer in the third phase;

providing the feature set generated by the first phase as input to the third phase, comprising providing the output of the non-linear activation function layer in the first phase as input to the fully connected layer in the third phase;

providing an output of the fully connected layer in the third phase to a softmax layer in the third phase; and outputting, by the softmax layer in the third phase, the third, binary classification;

wherein the second and third phases are trained to use transfer learning between the classifying the first cardiac event type in the first phase and the classifying the second and third cardiac event types in the second and third phases to classify the second and third cardiac events, wherein the second and third cardiac events occur at least partially at the same time as the first cardiac event, and wherein the classified first cardiac event and the classified second cardiac event are configured to be used in medical treatment of the patient.

14. The non-transitory computer-readable medium of claim 13, the operation further comprising:

classifying a fourth cardiac event, comprising a fourth cardiac event type different from the first and second and third cardiac event types, in the ECG data based on the classified first cardiac event, comprising:

providing the classified first cardiac event, and the feature set generated by the first phase, as input to a fourth phase in the machine learning architecture, wherein the fourth phase is trained to use transfer learning between the classifying the first cardiac event type in the first phase and the classifying the fourth cardiac event type in the fourth phase to classify the fourth cardiac event, wherein the fourth cardiac event occurs at least partially at the same time as the first cardiac event, and wherein the classifying the fourth cardiac event and the classifying the second and third cardiac events occur at least partially in parallel.

15. The non-transitory computer-readable medium of claim 13, wherein the second phase of the machine learning architecture is trained based on the first phase of the machine learning architecture.

16. The non-transitory computer-readable medium of claim 13, wherein the second phase of the machine learning architecture is trained at the same time as the first phase of the machine learning architecture.

* * * * *